US00PP36339P2

(12) United States Plant Patent
Meilland

(10) Patent No.: US PP36,339 P2
(45) Date of Patent: Dec. 31, 2024

(54) MINIATURE ROSE PLANT NAMED 'MEIPATEQ'

(50) Latin Name: *Rosa hybrida*
Varietal Denomination: MEIPATEQ

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/233,026

(22) Filed: Aug. 11, 2023

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122, 129
CPC ..... A01H 5/0222
See application file for complete search history.

(56) References Cited

U.S. PATENT DOCUMENTS

PP9,652 P 10/1996 Meilland
PP16,202 P2 1/2006 Radler

OTHER PUBLICATIONS https://issuu.com/starrosesandplants/docs/2024_rosecatalog; Mar. 1, 2023; 1 page.*
https://gpnmag.com/news/star-roses-and-plants-to-showcase-new-varieties-at-cultivate23/; Jul. 14, 2023; 2 pages.*
https://www.aldenlane.com/2022-miniature-roses; Sep. 29, 2022; 3 pages.*

* cited by examiner

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEIPATEQ', is disclosed. The new variety forms attractive, double, red colored flowers. Attractive dense, semi-glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEIPATEQ'.

STATEMENT REGARDING PRIOR DISCLOSURES BY THE INVENTOR

The first offer for sale of the new variety was Oct. 7, 2022, in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior to the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'MEINEYTA' variety (not patented). The male parent (i.e., the pollen parent) of the new variety was an unnamed seedling (not patented) which is the product of a cross between an unnamed seedling (not patented) and the 'RADTKO' variety (16,202).

The parentage of the new variety can be summarized as follows:

MEINEYTA' X (Unnamed Seedling X 'RADTKO')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms bright red colored flowers,
(b) produces double flowers, and
(c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEINEYTA' variety (i.e., the seed parent) produces salmon-colored flowers, whereas the new variety produces red colored flowers. In addition, the unnamed seedling male parent (i.e., pollen parent) forms flowers with less petals (semi-double) compared to the new variety which form flowers with more petals (double). Moreover, the new variety can be readily distinguished from other similar non-parental varieties. For example, the 'MEIFERJAC' variety (U.S. Plant Pat. No. 9,652) forms approximately 6 to 15 flowers per stem that have approximately 27 petals per flower, whereas the new variety forms typically 1 to 4 flowers per stem that typically have 35 to 40 petals per flower.

The new variety has been named 'MEIPATEQ'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately eighteen months of age and were observed during July while budded on *Rosa* 'Manetti' (not patented) and growing outdoors at Le Cannet des Maures, Var, France. Dimensions in centimeters are indicated at the bottom of the drawing.

Element 1—illustrates a specimen of a young shoot.
Element 2—illustrates a specimen of a floral bud before the opening of the sepals.
Element 3—illustrates a specimen of a floral bud at the opening of the sepals.
Element 4—illustrates a specimen of a floral bud at the opening of the petals.
Element 5—illustrates a specimen of a flower in the course of opening.
Element 6—illustrates a specimen of an open flower—plan view—obverse.
Element 7—illustrates a specimen of an open flower—plan view—reverse.
Element 8—illustrates a specimen of a fully open flower—plan view—obverse.
Element 9—illustrates a specimen of a fully open flower—plan view—reverse.
Element 10—illustrates a specimen of a floral receptacle showing arrangement of the stamens and pistils.
Element 11—illustrates a specimen of a floral receptacle showing arrangement of the pistils (stamens removed).
Element 12—illustrates a specimen of a flowering stem.
Element 13—illustrates a specimen of a leaf with 3 leaflets—plan view—upper surface.
Element 14—illustrates a specimen of a leaf with 3 leaflets—plan view—under surface.
Element 15—illustrates a specimen of a leaf with 5 leaflets—plan view—upper surface.
Element 16—illustrates a specimen of a leaf with 5 leaflets—plan view—under surface.
Element 17—illustrates a specimen of a leaf with 7 leaflets—plan view—upper surface.
Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The R.H.S. Colour Chart designation used herein represents the closest color observed on the majority of the specified botanical feature. The description is based on the observation of eighteen-months-old specimens of the new variety during July while budded on *Rosa* 'Manetti' (not patented) and growing outdoors at Le Cannet des Maures, Var, France.

Botanical classification: *Rosa hybrida* cultivar MEIPATEQ.
Commercial classification: Miniature Rose Plant.

Plant:
*Habit*.—Bushy.
*Height*.—Approximately 40 cm on average.
*Width*.—Approximately 40 cm on average.

Branches:
*Color*.—Young stems: Green Group 143A. — adult wood: a color between Green Group 137A and Green Group 143A.
*Length*.—From the crown to the flower is typically between 20 cm to 30 cm.
*Diameter*.—Typically between 0.4 cm to 0.8 cm.
*Thorns*.—Configuration on adult stems: concave, elongated and little curved downwards on the upper surface and concave on the under surface. — long prickles—quantity: approximately 6 thorns on average per 10 cm long young stem and approximately 7 thorns on average per 10 cm long adult stem. — long prickles—length: approximately 0.4 cm on average on young stems and typically between 0.5 cm to 0.8 cm on adult stems. — long prickles—width at base: typically between 0.3 cm to 0.5 cm on young stems and typically between 0.4 cm to 0.7 cm on adult stems. — long prickles—base shape: obovate, narrow, and long on young stems and oval, narrow, and long on adult stems. — long prickles—color on young stems: Yellow-Green Group 144C. — long prickles—color on adult stems: a color between Greyed-Orange Group 164B and Greyed-Orange Group 165B. — small prickles: absent.
*Internode*.—Numbers on the entire branch: typically between 5 to 8. — length: typically between 2.5 cm to 5.0 cm.

Foliage:
*General appearance*.—Dense, semi-glossy.
*Number of leaflets*.—3, 5, 7; most often 7.
7 *leaflets leaf*.—Length: typically between 7.0 cm to 11.0 cm. — width: typically between 4.0 cm to 7.0 cm.
*Terminal leaflet*.—Length: approximately 4.0 cm on average. — width: typically between 2.0 cm to 2.5 cm.
*Young shoots*.—Anthocyanin coloration: Greyed-Purple Group 183C.

*New foliage*.—Upper surface color: a color between Green Group 137A and Yellow-Green Group 146A. — under surface color: Green Group 137D.

*Adult foliage*.—Upper surface color: a color between Green Group 137A and Green Group 139A. — under surface color: Green Group 137C.

Leaflets:

*Shape*.—Tip: acuminate. — base: obtuse.

*Intensity of glossiness*.—Medium.

*Texture*.—Moderately leathery.

*Smoothness*.—Upper and under surfaces are smooth.

*General appearance*.—Elliptical.

*Serration*.—Small and single.

*Undulation on the margin*.—Medium.

*Venation*.—Color is a color between Green Group 137A and Green Group 139A and pattern is imparipinnate.

*Petiole rachis*.—Color of upper surface: Yellow-Green Group 145B in the middle and Green Group 143A on the edges. — color of under surface: Yellow-Green Group 144B. — texture: upper surface is glandular, under surface is very few little pickles (very few to none). — rachis of terminal leaflet: length is typically between 4.0 cm to 5.0 cm and diameter is approximately 0.1 cm on average.

*Petioles*.—Upper surface: glandular. — under surface: smooth. — color of upper surface: Yellow-Green Group 145B in the middle and Green Group 143A on the edges. — color of under surface: Yellow-Green Group 144B. — length: typically between 2.0 cm to 3.0 cm. — diameter: approximately 0.1 cm on average.

*Stipules*.—Length: typically between 1.5 cm to 2.0 cm. — width: typically between 0.5 cm to 0.8 cm. — general appearance: broad. — texture: smooth and glandular on the edges on upper and under surfaces. — color of upper surface: Yellow-Green Group 145B in the middle and Green Group 143A on the edges. — color of under surface: Yellow-Green Group 144B in the middle and Green Group 143A on the edges.

Inflorescence:

*Number of flowers per stem*.—Typically between 1 to 4 flowers per stem.

*Lastingness of the bloom*.—On the plant: approximately 15 days. — in vase: not tested.

*Bud*.—Shape: conical. — size: small. — length: approximately 1.5 cm on average. — width: approximately 1.0 cm on average. — color as calyx breaks: upper surface: a color between Red Group 44A and Red Group 45A; basal spot is Yellow Group 9A. under surface: Red Group 45C; basal is Yellow Group 8A.

*Sepals*.—Number. commonly 5. — length: typically between 1.5 cm to 2.0 cm. — width: approximately 0.5 cm on average. — shape: at the top: elongated and narrow. at the base: flat at union with the receptacle. — extensions: typically 2 sepals without extensions, 1 sepal with weak extension, and 2 sepals with medium extensions. — upper surface: texture: tomentous. color: Yellow-Green Group 144B suffused with Green Group 143A and covered with many hairs White Group 155B. — under surface: texture: glandular on the edges. color: Yellow-Green Group 144B suffused with Green Group 143A.

*Receptacle*.—Color: Yellow-Green Group 144A. — length: approximately 0.8 cm on average. — width: approximately 0.5 cm on average. — surface: smooth. — shape: pitcher shaped.

*Peduncle*.—Length: typically between 2.5 cm to 4.0 cm. — width: approximately 0.2 cm on average — surface: glandular. — color: a color between Yellow-Green Group 144A and 144B.

*Flower*.—Diameter when open: typically between 3.5 cm to 5.0 cm. — depth of the flower: approximately 1.5 cm on average. — shape: flat cup shaped. — shape when viewed from above: irregular rounded. — shape of the upper part of the flower profile: flat. — shape of the lower part of the flower profile: flat. — type: double. — number of petals under normal conditions: typically between 35 to 40. — petals: general shape: external petals are rounded; internal petals are elliptic. shape at the base: obtuse. shape at the top: rounded. texture: thick. length: external petals are approximately 1.5 cm on average; internal petals are typically between 1.0 cm to 1.5 cm. width: external petals are approximately 1.5 cm on average; internal petals are typically between 0.5 cm to 1.0 cm. — undulation of the petal: strong. — reflexing of the petal: weak. — petal incision: very weak. — petal arrangement: imbricated with some petaloids (appear as crumbled internal petals). — petal drop: petals drop off cleanly before drying. — fragrance: none. — discoloration of the flower: turns to dark pink color Red-Purple Group 57A. — color when opening: basal spot on the upper surface: Yellow Group 9B. upper surface: Red Group 45B. basal spot on the under surface: Yellow Group 8A. under surface: Red Group 45C. — color of the open flower: basal spot on upper surface: Yellow Group 8B. upper surface: Red Group 45C. basal spot on under surface: Yellow Group 8C. under surface of the flower: Red Group 45D. — anthers: approximately 50 on average, length is approximately 0.1 cm on average, width is approximately 0.1 cm on average, coloration is Yellow-Orange Group 15A, and arrangement is regular around styles. — filaments: length is typically between 0.3 cm to 0.4 cm and coloration is Yellow-Orange Group 15B. — styles: length is typically between 0.5 cm to 0.7 cm, coloration is Green-White Group 157A at the base part and Red-Purple Group 57A on the upper part, and number is approximately 25 on average. — stigmas: length is typically less than 0.1 cm and coloration is Yellow-Orange Group 22C. — pollen: low quantity; color is Yellow Group 3D. — hips: not produced to date.

Development:

*Vegetation*.—Strong.

*Blooming*.—Early in the season abundant and nearly continuous, typically from May to October in France.

*USDA hardiness zone*.—Tested to Zone 5.

*Tolerance to disease*.—Good, and particularly against rust (*Phragmidium* sp.).

The new 'MEIPATEQ' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIPATEQ' characterized by the following combination of characteristics:

(a) forms bright red colored flowers, (b) produces double flowers, and (c) exhibits a bushy growth habit;

substantially as herein shown and described.

* * * * *

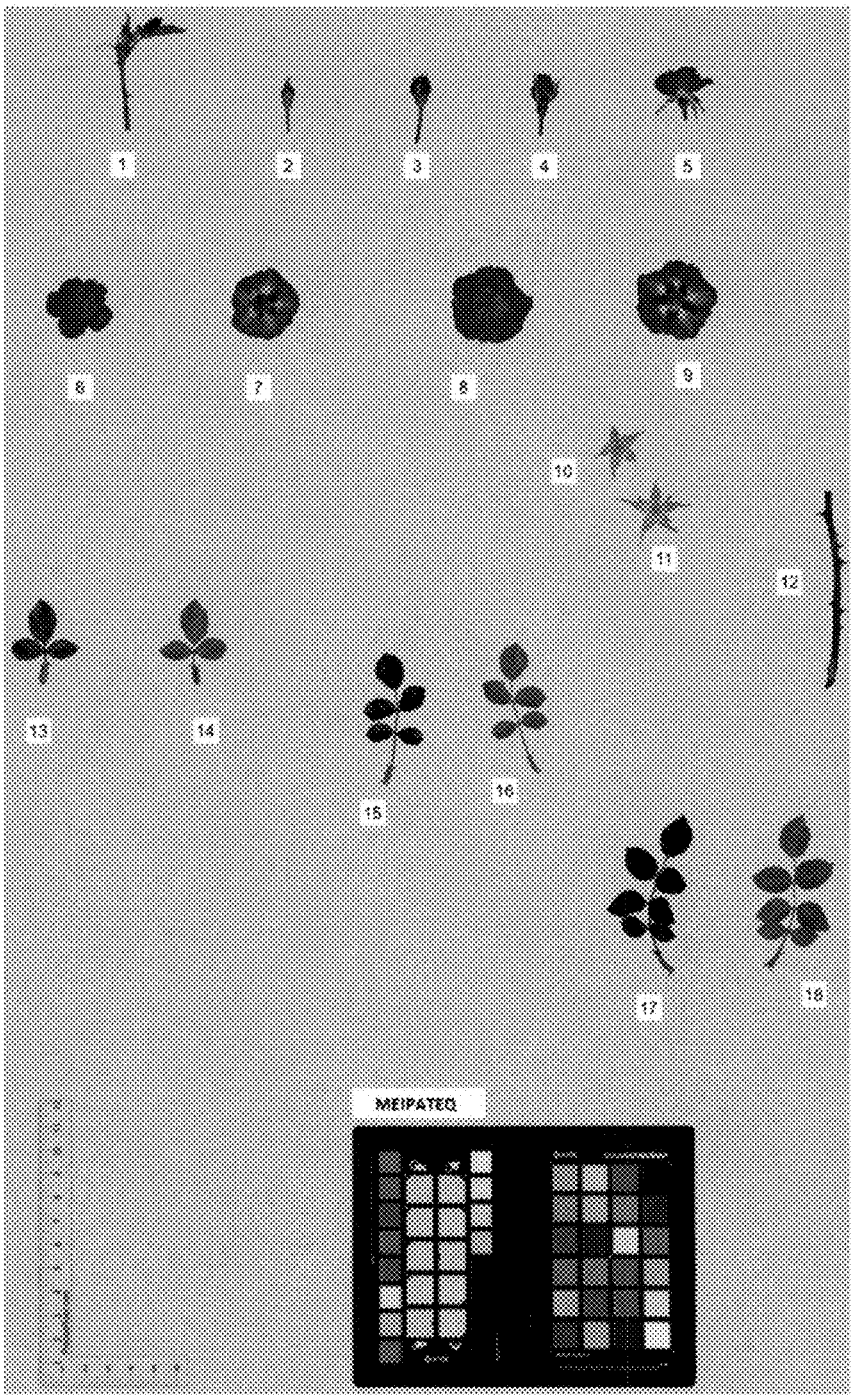
1
2
3
4
5
6
7
8
9
10
11
12
13
14
15
16
17
18
MEIPATEQ